(12) United States Patent
Xu et al.

(10) Patent No.: US 6,627,578 B2
(45) Date of Patent: Sep. 30, 2003

(54) CATALYST FOR SELECTIVE HYDROGENATION

(75) Inventors: Liying Xu, Beijing (CN); Yunxian Zhu, Beijing (CN); Yi Yue, Beijing (CN); Lingke Kong, Beijing (CN); Shusheng Gao, Beijing (CN)

(73) Assignees: China Petro-Chemical Corporation, Beijing (CN); Beijing Research Institute of Chemical Industry, Beijing (CN)

( * ) Notice: Subject to any disclaimer, the term of this patent is extended or adjusted under 35 U.S.C. 154(b) by 358 days.

(21) Appl. No.: 09/845,534

(22) Filed: Apr. 30, 2001

(65) Prior Publication Data
US 2002/0025907 A1 Feb. 28, 2002

(30) Foreign Application Priority Data
Apr. 30, 2000 (CN) ..................................... 00 1 07257 A

(51) Int. Cl.$^7$ ................................................ B01J 23/72
(52) U.S. Cl. ....................... 502/331; 502/333; 502/345; 585/260
(58) Field of Search ................................. 502/304, 311, 502/313, 315, 318, 320, 322, 324, 327, 331, 346, 335, 334, 333; 585/260

(56) References Cited

U.S. PATENT DOCUMENTS

| | | | |
|---|---|---|---|
| 4,101,451 A | 7/1978 | Frevel et al. ................ 252/465 |
| 5,145,587 A * | 9/1992 | Ishii et al. ................... 210/759 |
| 5,347,046 A * | 9/1994 | White et al. ................. 560/245 |
| 5,414,201 A * | 5/1995 | Greene ........................ 588/206 |
| 5,516,851 A | 5/1996 | Flick et al. ............... 525/330.2 |
| 5,648,576 A | 7/1997 | Nguyen Than et al. ..... 585/260 |

FOREIGN PATENT DOCUMENTS

| | | |
|---|---|---|
| EP | 0139051 | 5/1985 |
| EP | 0985447 | 3/2000 |
| EP | 0992284 | 4/2000 |
| GB | 802100 | 10/1958 |
| JP | 57185228 | 11/1982 |

OTHER PUBLICATIONS

Patent Abstracts of Japan of JP 57–185228 dated Nov. 15, 1982.
Patent Abstract of Japan Publication No.: 58210854 Dated Dec. 8, 1983.

* cited by examiner

Primary Examiner—Stanley S. Silverman
Assistant Examiner—Edward M. Johnson
(74) Attorney, Agent, or Firm—Ladas & Parry

(57) ABSTRACT

A catalyst for selective hydrogenation, which comprises, on the basis of the total weight of catalyst, 1–30 wt % of copper as the first active component, 0.001–5 wt % of palladium as the second active component, 0.001–6 wt % of at least one metal selected from Ag, Pt, Pb, Mn, Co, Ni, Cr, Bi, Zr and Mo as cocatalyst, and the balance of at least one support selected from alumina, silica or titania. The present invention further relates to its preparation, its use in removal of alkynes from alkyne-enriched $C_4$ cuts through selective hydrogenation and its regeneration.

31 Claims, No Drawings

CATALYST FOR SELECTIVE HYDROGENATION

The present invention relates to a catalyst for hydrogenation, more particularly, it relates to a catalyst for the selective hydrogenation of alkynes in $C_4$ cuts. The present invention also relates to a process for the preparation of the said catalyst, its use in the selective hydrogenation and a regeneration method of the said catalyst.

The $C_4$ cuts produced in petrochemical industry represents a mixture of several alkanes and olefins containing 4 carbon atoms, in which 1,3-butadiene, deemed as one of the industrially valuable component, accounts to about 40–60 wt %, and the alkynes present as impurities, including methyl acetylene (MA), ethyl acetylene (EA) and vinyl acetylene (VA) etc., amounts to 0.5–2.5 wt %. Therefore, there is a need to hydrogenate alkynes in $C_4$ cuts to obtain 1,3-butadiene in high purity that meets the requirements of polymerization.

One of the methods for removing alkynes is based on catalytically selective hydrogenation of alkynes by means of catalysts in such a way as to convert the alkynes, such as VA, EA, MA etc. into butadiene, butene and butane although the latter form is in a relatively small amount, thus making the $C_4$ alkynes become valuable. The catalyst for hydrogenation used in such a alkyne-removing method should have high activity and selectivity and thereby can remove alkynes effectively while minimizing the 1,3-butadiene losses. In addition, it is desirable that the catalyst has a good running stability over time with low operation investment.

U.S. Pat. No. 4,101,451, filed on Jan. 19, 1977 and thereafter issued to The Dow Chemical Company, disclosed a process for improving the activity of a promoted copper catalyst suitable for selectively hydrogenating alkynes in liquid streams containing olefins. In the working examples of this parent, use was made of the catalyst in which the salts of Cu, Ni, Co, Cr, Mn or Ag were supported on the supporting material of α-alumina containing $Na_2O$.

JP57-185,228 disclosed a process for selective hydrogenation of alkyne compounds. The catalysts comprising $Al_2O_3$ as a support, and palladium and copper or palladium and silver as active components were used in its examples to hydrogenate alkynes in $C_4$ cuts.

It appears that when the catalysts which are widely adopted in the prior art are used in the removal of alkynes from $C_4$ cuts through selective hydrogenation, problems arise from the impossibility of selective hydrogenation in an efficient way of alkyne-enriched $C_4$ cuts in which the alkyne content is, for example up to 2 wt % on the one hand, and unlikeliness of complete hydrogenation to obtain satisfactory removal of alkynes for example to the extent of 25 ppm, or even 15 ppm in alkyne content as required in the process specification in the art on the other hand. Therefore, it is necessary to seek for a catalyst which can remove alkynes from alkyne-enriched $C_4$ cuts through selective hydrogenation steadily and efficiently.

Accordingly, it is an object of the present invention to provide a novel catalyst, which can be used to remove alkynes from alkyne-enriched $C_4$ cuts through selective hydrogenation with high efficiency, good selectivity, prominent stability and a long life time.

It is another object of the present invention to provide a process for preparing a catalyst, which can be used to remove alkynes from alkyne-enriched $C_4$ cuts through selective hydrogenation with high efficiency, good selectivity, prominent stability and a long life time.

It is still another object of the present invention to provide a use of the said catalyst in respect of removal of alkyne, from alkyne-enriched $C_4$ cuts through selective hydrogenation.

It is yet a further object of the present invention to provide a process for regenerating the above-mentioned catalyst.

These and other objects are accomplished by providing in a surprising and unexpected manner a catalyst, comprising 1–30 wt % of copper as a first active component, 0.001–5 wt % of palladium as a second active component, 0.001–6 wt % of at least one metal selected from Ag, Pt, Pb, Mn, Co, Ni, Cr, Bi, Zr and Mo as a cocatalyst, and the balance of at least one support selected from alumina, silica and titania, all the percentage indicated hereinabove and hereinafter are calculated on the basis of total weight of the catalyst except those otherwise designated.

Preferably, the catalyst according to the present invention comprises 3–20 wt % of copper, 0.05–3 wt % of palladium, 0.01–4 wt % of at least one metal selected from Ag, Pt, Pb, Mn, Co, Ni, Cr, Bi, Zr and Mo as a cocatalyst, based on the total weight of the catalyst.

More preferably, the catalyst according to the present invention comprises 3–20 wt % of copper, 0.05–1 wt % of palladium, 0.01–1 wt % of at least one metal selected from Ag, Pt, Pb, Mn, Co, Ni, Cr, Bi, Zr and Mo as a cocatalyst, based on the total weight of the catalyst.

As a variant of the present invention, the weight ratio of Cu/Pd in the final catalyst is in the range of from 20–60.

As a variant of the present invention, the support used in the catalyst of the present invention is optionally treated with alkali metal salts, alkaline earth metal salts of mixtures thereof so as to enhance the catalyst selectivity and lower the surface acidity of the support and thereby control the polymerization of butadiene by reducing the possible buildup of polymers.

Preferably, the said alkali meal is selected from at least one of the group consisting of Li, Na, K, Rb and Cs, and the said alkaline earth metal is selected from at least one of the group consisting of Be, Mg, Ca, Sr and Ba.

More preferably, the said alkali metal is selected from at least one of the group consisting of Li, Na and K, and the said alkaline earth metal is selected from at least one of the group consisting of Dc, Mg and Ca.

Preferably, the amount of said alkali metal salts, alkaline earth metal salts or mixtures thereof expressed in terms of the elementary metal is 0.001–3 wt %, preferably 0.05–0.5 wt %, based on the total weight of the catalyst, The catalyst according to the present invention has a specific surface area of 100–350 $m^2/g$, as determined by means of model BC-1 surface area measuring instrument.

The catalyst according to the present invention has an average pore diameter of 30–200 Å, as determined by means of Absorption Detector of the type Sorptomatic 1990 (Ex FISONS Corp.) in which $N_2$ is used as an absorption gas.

Preferably, alumina, titania or silica in the form of bars, strips, platelets, cylindrical granulae, granular powders or spheroidal particle is used as a support in the catalyst of the present invention.

More preferably, alumina, titania or silica in the form of spheroidal particle of Φ2–5 mm is preferably used as a support in the present catalyst.

The present invention further relates to the process for preparing the catalyst according to the present invention, comprising the steps of;

(1) The support-forming substance selected from at least one of alumina, silica or titania is calcined at 200–900° C.;

(2) The support resulting from step (1) is impregnated in any order in a copper nitrate solution and a palladium nitrate, palladium chloride or palladium acetate solution to the extent that the copper content reaches 1–30 wt % and palladium content is 0.001–5 wt %, based on the total weight of the catalyst;

(3) The pH value of the palladium nitrate, palladium chloride or palladium acetate solution used in step (2) is adjusted to 3–6 with aqueous ammonia, sodium bicarbonate or sodium carbonate solutions;

(4) The support obtained from step (2) is calcined at 300–500° C. for 4–10 hours;

(5) The support is impregnated in any order with a solution of salt of at least one metal selected from Ag, Pt Pb, Mn, Co, Ni, Cr, Bi, Zr and Mo as a cocatalyst simultaneously with or independently of the copper salt solution in step (2).

In accordance with a variant of the process according to the present invention, the said support is formed into bars, strips, platelets, cylindrical granulae, granular powders or spheroidal particles, preferably spheroidal particles.

More preferably, alumina, titania, or silica in the form of spheroidal particles of Φ2–5 mm are used as a support in the process for preparation of the catalyst according to the present invention.

In accordance with a variant of the process according to the present invention, in step (1), the support-forming substance is calcined at 300–800° C. for 1–8 hours.

In accordance with a variant of the process according to the present invention, in step (3), the pH is adjusted to 3~5 with aqueous ammonia or solutions of sodium bicarbonate or sodium carbonate.

In accordance with a variant of the process according to the present invention, the support is impregnated in any order with a solution of salt of at least one metal selected from Ag, Pt, Bi, Pb and Zr as a cocatalyst simultaneously with or independently of the copper salt solution in step (2).

In accordance with a variant of the process according to the present invention, in step (2), the support is impregnated in solutions of palladium nitrate, palladium chloride or palladium nitrate preferably after having been impregnated in the copper nitrate solution.

In accordance with a variant of the process according to the present invention, after step (1), it optionally comprises a step of impregnating the support obtained from the step (1) in the alkali or alkaline earth metal salt solution or mixtures thereof.

In accordance with a variant of the process according to the present invention, the weight ratio of Cu/Pd in the final catalyst is in the range of from 20 to 60.

It is preferred that the alkali metal salts alkaline earth metal salts or mixtures thereof expressed in terms of elementary metal accounts to 0.001–3 wt %, preferably 0.05~0.5 wt %, based on the total weight of the catalyst.

In accordance with the process according to the present invention, after having been impregnated with solutions of alkali or alkaline earth metal salt or mixtures thereof, the resulting support is dried and then calcined at 350–500° C. for 6–10 hours.

The present invention further relates to the use of the catalyst according to the present invention in respect of the removal of alkynes from alkyne-enriched $C_4$ cuts through selective hydrogenation, which comprises passing the $C_4$ cuts with 0.5–2.5 wt % of alkynes and hydrogen gas into a fixed bed which is loaded with the catalyst according to the present invention, wherein the inlet temperature is within the range of from 20–50° C., the reaction pressure ranges from 0.6–1.0 MPa, the liquid hourly space velocity (LHSV) is set at 2–60 $h^{-1}$ (vol./vol.), and the molar ratio of hydrogen to alkynes is ranging from 1–6.

According to a variant of the use of the catalysts according to the present invention, as regards the alkynes which can be removed through selective hydrogenation using the catalysts according to the present invention, mention may be made of methyl acetylene, ethyl acetylene and vinyl acetylene.

According to a variant of the use of the present catalysts, as regards the fixed bed as used, reference may be made to one-stage bed, double-stage bed or any other conventional catalyst beds in the art suitable for prolonging the catalyst life time.

By the wording "alkyne-enriched" throughout the whole text of the present application is meant such a content of alkyne that reaches as high as 2.5 wt % of the $C_4$ cuts to be treated.

The present invention will be further illustrated with reference to the following examples, but these examples are not construed with limiting the present invention. The protection scope sought for by the present invention is defined by the appended claims.

Preparation of the Catalyst

The commercially available spheroidal particles of $Al_2O_3$ or $TiO_2$ of Φ 2–3 mm were calcined at 636° C. for 6 hours, then optionally impregnated in the solution of alkali or alkaline earth metal salt. The resulting support was dried and calcined at 350° C. for 6 hours and then, impregnated in a formulated solution of copper nitrate to the extent that the copper content is 1–30 wt %, based on the total weight of the catalyst. The resulting support was calcined at 300–600° C. for 4–10 hours. Then the resulting support was impregnated in the formulated solutions of palladium nitrate, palladium chloride or palladium acetate of which pH had been adjusted to 3~5 with aqueous ammonia or solutions of sodium bicarbonate or sodium carbonate to the extent that the obtained product contains 0.001–5 wt % of palladium with the weight ratio of Cu/Pd in the final catalyst ranging from 20–60, based on the total weight of the catalyst. Again the support was calcined at 350° C. for 6 hours. The support was impregnated in any order in a solution of salt of at least one metal as a cocatalyst selected from the group consisting of Ag, Pt, Pb, Mn, Co, Ni, Cr, Bi, Zn and Mo simultaneously with or independently of the above mentioned copper nitrate solution. The strength of the catalyst particles is of 0.6–1.0 MPa per particle.

In the examples, the hydrogenation was carried out in a fixed bed reactor which operates at the following parameters:

| Inlet temparature (° C.) | 20–50 |
| --- | --- |
| Reaction pressure (MPa) | 0.6–1.0 |
| LHSV ($h^{-1}$, vol./vol.) | 2–60 |
| $H_2$/alkynes (mol/mol) | 1–6 |

The experiment conditions and results are assembled in table 1 deprived of the first active component Cu was investigated in example 14. The performance of the catalyst not containing the selected cocatalyst according to the present invention such as Ag was investigated in example 15. The performance of the catalyst not having the second active component Pd was investigated in example 16. In comparison to each other, the test results obtained by using the catalysts of the above-mentioned 3 comparative examples and that of example 13 representing the present invention are listed in table 2, indicating the respective changes in respect of residual alkyne contents and butadiene losses over time in each case.

TABLE 1

The composition of catalysts and their effects

| Example | Cu wt % | Pd wt % | Cocatalysts and contents thereof wt % | Nature of suppor. | Alkali or alkaline earth metals and their amounts used wt % | Alkynes in feedstocks wt % | Reaction time h | Residual alkynes ppm | Butadiene loss wt % | $H_2$/alkyne mol/mol | LHSV $h^{-1}$ (vol/vol) | Catalyst change ml |
| --- | --- | --- | --- | --- | --- | --- | --- | --- | --- | --- | --- | --- |
| 1 | 11.3 | 0.2 | Ag: 0.2 | $Al_2O_3$ | — | 0.9 | 592 | <15 | <1.40 | 4 | 5 | 30 |
| 2 | 13.5 | 0.2 | Ag: 0.2 | $TiO_2$ | — | 0.9 | 196 | <21.3 | <2.00 | 4 | 6 | 30 |
| 3 | 9.8 | 0.1 | Ag: 0.1 | $Al_2O_3$ | Na: 0.2 | 0.7 | 182 | 0 | <0.85 | 3 | 4 | 30 |
| 4 | 14.6 | 0.2 | Ag: 0.3 | $Al_2O_3$ | K: 0.1 | 0.7 | 129 | 0 | <1.62 | 3 | 4 | 30 |
| 5 | 14.6 | 0.2 | Ag: 0.2 | $Al_2O_3$ | Ca: 0.2 | 0.7 | 103 | <13 | <2.45 | 3 | 4 | 30 |
| 6 | 13.8 | 0.1 | — | $Al_2O_3$ | K: 0.1; Mg: 0.1 | 0.7 | 138 | <18.9 | <2.1 | 3 | 4 | 30 |
| 7 | 11.4 | 0.15 | Zr: 0.1 | $Al_2O_3$ | — | 0.9 | 329 | <16 | <1.47 | 4 | 4 | 20 |
| 8 | 10.4 | 0.15 | Pb: 0.2 | $Al_2O_3$ | — | 0.9 | 73 | <100 | <3.79 | 6 | 12 | 20 |
| 9 | 13.8 | 0.15 | Bi: 1.0 | $Al_2O_3$ | — | 0.7 | 62 | <16.4 | <0.85 | 4 | 5 | 20 |
| 10 | 12.8 | 0.15 | Ag: 0.3 | $Al_2O_3$ | — | 0.7 | 98 | <20 | <2.47 | 4 | 5 | 20 |
| 11 | 5.6 | 0.8 | — | $Al_2O_3$ | — | 0.6 | 142 | <98 | <1.80 | 3 | 4 | 30 |
| 12 | 157 | 0.15 | — | $Al_2O_3$ | — | 0.6 | 58 | 0 | <3.19 | 3 | 4 | 30 |
| 13 | 134 | 0.15 | Ag: 0.1 | $Al_2O_3$ | — | 1.3 | 1000 | <13 | <1.20 | 2 | 4 | 200 |
| 14 | 0 | 0.2 | Ag: 0.1 | $Al_2O_3$ | — | 0.6 | 53 | <4500 | 1.10 | 1.5 | 10 | 30 |
| 15 | 10.4 | 0.3 | 0 | $Al_2O_3$ | — | 0.6 | 64 | <199 | <3.50 | 6 | 10 | 30 |
| 16 | 8.50 | 0 | Ag: 0.1 Pb: 0.1 Zr: 0.1 Ni: 0.1 Co: 0.1 | $Al_2O_3$ | — | 0.6 | 40 | <1100 | <4.10 | 6 | 6 | 30 |
| 17 | 13.1 | 0.17 | Ag: 0.1 | $Al_2O_3$ | — | 0.8 | 145 | <4700 | <0.65 | 1.2 | 30 | 30 |

As shown in table 1, examples 7 and 13 were carried out in a double-stage fixed bed reactor. Examples 14, 15 and 16 constitute comparative tests. The performance of the catalyst

TABLE 2

The changes in respect of residual alkynes content and butadiene loss over time

| Example 13 | | | Example 14 | | | Example 15 | | | Example 16 | | |
| --- | --- | --- | --- | --- | --- | --- | --- | --- | --- | --- | --- |
| overall reaction time h | residual alkynes content ppm | butadiene loss wt % | overall reaction time h | residual alkynes content ppm | butadiene loss wt % | overall reaction time h | residual alkynes content ppm | butadiene loss wt % | overall reaction time h | residual alkynes content ppm | butadiene loss wt % |
| 42 | 12.2 | 0.88 | 7 | 1000 | 1.07 | 8 | 100 | 1.78 | 7 | 1000 | 1.08 |
| 110 | 12.8 | 0.62 | 16 | 1400 | 1.09 | 16 | 158 | 3.18 | 16 | 900 | 1.35 |
| 155 | 11.7 | 0.54 | 25 | 1900 | 0.61 | 22 | 112 | 3.48 | 20 | 95 | 2.95 |
| 207 | 8.1 | 0.53 | 32 | 3400 | 0.09 | 32 | 56 | 2.35 | 25 | 112 | 4.10 |
| 243 | 8.5 | 1.24 | 40 | 3700 | 0.39 | 40 | 67 | 2.94 | 32 | 103 | 3.17 |
| 303 | 0.0 | 1.07 | 47 | 3500 | 0.79 | 48 | 130 | 2.48 | 37 | 50 | 2.34 |
| 343 | 0.0 | 1.20 | 53 | 4500 | 0.28 | 54 | 163 | 2.39 | 40 | 1100 | 1.25 |
| 395 | 9.8 | 0.38 | | | | 64 | 199 | 1.65 | | | |
| 447 | 6.7 | 0.60 | | | | | | | | | |
| 507 | 0.0 | 0.97 | | | | | | | | | |
| 559 | 10.5 | 1.15 | | | | | | | | | |
| 603 | 4.9 | 0.91 | | | | | | | | | |
| 647 | 12.4 | 1.12 | | | | | | | | | |

TABLE 2-continued

The changes in respect of residual alkynes content and butadiene loss over time

| Example 13 | | | Example 14 | | | Example 15 | | | Example 16 | | |
| --- | --- | --- | --- | --- | --- | --- | --- | --- | --- | --- | --- |
| overall reaction time h | residual alkynes content ppm | butadiene loss wt % | overall reaction time h | residual alkynes content ppm | butadiene loss wt % | overall reaction time h | residual alkynes content ppm | butadiene loss wt % | overall reaction time h | residual alkynes content ppm | butadiene loss wt % |
| 703 | 6.7 | 0.87 | | | | | | | | | |
| 747 | 8.5 | 0.65 | | | | | | | | | |
| 807 | 5.1 | 0.72 | | | | | | | | | |
| 847 | 10.7 | 0.65 | | | | | | | | | |
| 907 | 7.3 | 0.83 | | | | | | | | | |
| 957 | 5.1 | 0.46 | | | | | | | | | |
| 1000 | 6.2 | 1.14 | | | | | | | | | |

As can be seen from table 1, the catalyst according to the present invention can be used to treat alkyne-enriched $C_4$ cuts and the alkyne content in the treated $C_4$ cuts can be reduced to below 15 ppm and 1,3-butadiene losses to below 1.5 wt %. The data in comparative example 14 indicates that palladium-based catalyst free of copper has low activity and the content of alkynes in the treated $C_4$ cuts is still as high as 4500 ppm. The comparative example 16 shows that the copper-based catalyst free of palladium has a slightly higher activity than that in example 14, which is still very low with a significant loss of 1,3-butadiene. The comparative example 15 shows that the activity of copper-based catalyst can be significantly enhanced by addition of palladium. The example 13 indicates that the activity of copper-palladium catalyst can be improved greatly by addition of a cocatalyst component and the loss of 1,3-butadiene can be further reduced as compared to comparative example 15.

From table 2, it comes to light that the catalyst in the art suffers from low activity and a short life time as well, while the activity and selectivity of the catalysts according to the present invention can be maintained well after long run.

The catalyst provided by the present invention demonstrates both the advantages of non-noble metal copper-based catalysts and noble metal palladium-based catalysts by getting rid of their respective disadvantages. Firstly, the catalyst according to the present invention has such a high activity that even alkyne-enriched (0.5–2.5 wt %) $C_4$ cuts can be efficiently hydrogenated. In contrast, the catalysts commonly used in the prior art can only be used in selectively hydrogenating the $C_4$ cuts in which the alkyne content is below 0.2 wt %. Secondly, the catalyst according to the present invention has a good selectivity, i.e. none or hardly any of butadiene is subjected to hydrogenation during the course of the hydrogenation of alkynes. Thirdly, the surface acidity of the present support can be reduced efficiently by treatment of support with alkali metal salts, alkaline earth metal salts or mixtures thereof, which contributes to inhibiting the polymerization of dienes and reducing the build-up of polymers, thus reducing the loss of butadiene. Furthermore, the present catalyst has a long life time and regenaration period, and can be regenerated in a simple way to recover its initial activity.

It will be evident to those skilled in the art that the invention is not limited to the details of the foregoing illustrative examples and that the present invention may be embodied in other specific forms without departing from the essential attributes thereof, and all changes which come within the meaning and range of equivalency of the claims are therefore intended to be embraced therein.

What is claimed is:

1. A catalyst for selective hydrogenation, comprising on the basis of the total weight of the catalyst, 1–30 wt % of copper as a first active component, 0.001–5 wt % of palladium as a second active component, 0.001–6 wt % of at least one metal selected from Ag, Pt, Pb, Mn, Co, Ni, Cr, Bi, Zr and Mo as a cocatalyst, and the balance of at least one support selected from alumina, silica and titania.

2. A catalyst according to claim 1, which comprises 3–20 wt % of copper, 0.05–3 wt % of palladium, 0.01–4 wt % of at least one metal selected front Ag, Pt, Pb, Mn, Co, Ni, Cr, Bi, Zr and Mo as a cocatalyst, based on the total weight of the catalyst.

3. A catalyst according to claim 1, which comprises 3–20 wt % of copper, 0.05–1 wt % of palladium, 0.01–1 wt % of at least one metal selected from Ag, Pt, Pb, Mn, Co, Ni, Cr, Bi, Zr and Mo as a cocatalyst, based on the total weight of the catalyst.

4. A catalyst according to claim 1, wherein the said support is treated with alkali metal salts, alkaline earth metal salts or mixtures thereof.

5. A catalyst according to claim 4, wherein the said alkali metal is selected from at least one of the group consisting of Li, Na, K, Rb and Cs, and the said alkaline earth metal is selected from at least one of the group consisting of Be, Mg, Ca, Sr and Ba.

6. A catalyst according to claim 5, wherein the said alkali metal is selected from at least one of the group consisting of Li, Na and K, and the said alkaline earth metal is selected from at least one of the group consisting of Be, Mg and Ca.

7. A catalyst according to claim 4, wherein the said alkali metal salts, alkaline earth metal salts or mixtures thereof expressed in terms of the elementary metal accounts to 0.001–3 wt %, based on the total weight of the catalyst.

8. A catalyst according to claim 7, wherein the said alkali metal salts, alkaline earth metal salts or mixtures thereof expressed in terms of the elementary metal accounts to 0.05–0.5 wt %, based on the total weight of the catalyst.

9. A catalyst according to claim 1, wherein the weight ratio of Cu/Pd in the final catalyst is in the range of from 20 to 60.

10. A catalyst according to claim 1, which has a specific surface area of 100–350 m²/g.

11. A catalyst according to claim 1, which has an average pore diameter of 30–200 Å.

12. A catalyst according to claim 1, wherein the said support comprises alumina, silica or titania in the form of bars, strips, platelets, cylindrical granulae, granular powders, or spheroidal particles.

13. A catalyst according to claim 1, wherein the said support comprises alumina, titania or silica in the form of spheroidal particles of Φ 2–5 mm.

14. A process for preparing the catalyst according to claim 1, which comprises the steps of:
 (i) selecting the support-forming substance from at least one of alumina, silica or titania, and calcining at 200–900° C.;
 (ii) impregnating the support resulting from step(1) in any order in a copper nitrate solution and a palladium nitrate, palladium chloride or palladium acetate solution to the extent that the copper content reaches 1–30 wt % and palladium content is 0.001–5 wt %, based on the total weight of the catalyst;
 (iii) adjusting the pH value of the palladium nitrate, palladium chloride or palladium acetate solution used in step (2) to 3–6 with aqueous ammonia or a sodium bicarbonate or sodium carbonate carbonate solution;
 (iv) calcining the support obtained from step (2) at 300–500° C. for 4–10 hours;
 (v) impregnating the support in any order with a solution of salt of at least one metal selected from Ag, Pt, Pb, Mn, Co, Ni, Cr, Bi, Zr and Mo as a cocatalyst simultaneously with or independently of the copper salt solution in step (2).

15. A process according to claim 14, wherein the said support is formed into bars, stripe, platelets, cylindrical granulae, granular powders or spheroidal particles.

16. A process according to claim 14, wherein alumina, titania, or silica of Φ2–5 mm in the form of spheroidal particles are used as a support.

17. A process according to claim 14, wherein in step (1), the support-forming substance is calcined at 300–800° C. for 1–8 hours.

18. A process according to claim 14, wherein in step (3), the pH of the palladium nitrate, palladium chloride or palladium acetate solution is adjusted to 3–5 with aqueous ammonia or solutions of sodium bicarbonate or sodium carbonate.

19. A process according to claim 14, wherein the support is impregnated in any order with a solution of salt of at least one metal selected from Ag, Pt, Pb, Bi and Zr as a cocatalyst simultaneously with or independently of the copper salt solution in step (2).

20. A process according to claim 14, wherein in step (2), the support is impregnated in solutions of palladium nitrate, palladium chloride or palladium acetate after having been impregnated in the copper nitrate solution.

21. A process according to claim 14, which further comprises after step (1), a step of impregnating the support obtained from the step (1) in a alkali or alkaline earth metal salt solution or mixtures thereof.

22. A process according to claim 21, wherein the said alkali metal is selected from at least one of the group consisting of Li, Na, K, Rb and Ce, and the said alkaline earth metal is selected from at least one of the group consisting of Be, Mg, Ca, Si and Ba.

23. A process according to claim 22, wherein the said alkali metal is selected from at least one of the group consisting of Li, Na and K, and the said alkaline earth metal is selected from at least one of the group consisting of Be, Mg and Ca.

24. A process according to claim 21, wherein the alkali metal salts, alkaline earth metal salts or mixtures thereof expressed in terms of elementary metal accounts to 0.001–3 wt %, based on the total weight of the catalyst.

25. A process according to claim 24, wherein the alkali metal salts, alkaline earth metal salts or mixtures thereof expressed in terms of elementary metal accounts to 0.05–0.5 wt %, based on the total weight of the catalyst.

26. A process according to claim 21, wherein after having been impregnated with alkali metal or alkaline earth metal salt solutions or mixtures thereof, said support is dried and then calcined at 350–500° C. for 6–10 hours.

27. A process according to claim 14, wherein the weight ratio of Cu/Pd in the final catalyst is in the range of from 20 to 60.

28. A method for the removal of alkynes from alkyne-enriched $C_4$ cuts through selective hydrogenation, which comprises passing the $C_4$ cuts with 0.5–2.5 wt % of alkynes and hydrogen gas into a fixed bed which is loaded with the catalyst according to claim 1, wherein the inlet temperature is within the range of from 20–50° C., the reaction pressure ranges from 0.6–10 MPa, the liquid hourly space velocity is set at 2–60 $h^{-1}$ (vol/vol), and the molar ratio of hydrogen to alkynes ranges from 1–6.

29. The method according to claim 28, wherein the alkynes which are removed through selective hydrogenation using the catalyst are methyl acetylene, ethyl acetylene and vinyl acetylene.

30. The method according to claim 28, wherein the fixed bed is a one-stage bed, double-stage bed or other catalyst bed suitable for prolonging the catalyst life.

31. The method according to claim 28, wherein the liquid hourly space velocity in the fixed bed charged with the catalyst is in the range of from 2 to 40 $h^{-1}$ (vol/vol).

* * * * *